(12) United States Patent
Dröschel et al.

(10) Patent No.: US 7,572,489 B2
(45) Date of Patent: Aug. 11, 2009

(54) METHOD FOR IMMOBILIZING HYDROGEL-FORMING POLYMERS ON POLYMER SUBSTRATE SURFACES

(75) Inventors: Stefan Dröschel, Saarbrücken (DE); Rainer Fislage, St. Wendel (DE)

(73) Assignee: Fresenius Medical Care Deutschland GmbH, Bad Homberg (DE)

( * ) Notice: Subject to any disclaimer, the term of this patent is extended or adjusted under 35 U.S.C. 154(b) by 796 days.

(21) Appl. No.: 10/522,093

(22) PCT Filed: Jul. 24, 2003

(86) PCT No.: PCT/EP03/08180

§ 371 (c)(1), (2), (4) Date: Jan. 21, 2005

(87) PCT Pub. No.: WO2004/026356

PCT Pub. Date: Apr. 1, 2004

(65) Prior Publication Data

US 2005/0244647 A1 Nov. 3, 2005

(30) Foreign Application Priority Data

Aug. 22, 2002 (DE) ................................ 102 38 559

(51) Int. Cl.
*B32B 27/36* (2006.01)

(52) U.S. Cl. ..................... 427/547; 428/412; 428/423.1

(58) Field of Classification Search .................. 427/547
See application file for complete search history.

(56) References Cited

U.S. PATENT DOCUMENTS

| 4,766,160 A | 8/1988 | Bichon et al. |
| 6,410,645 B1 | 6/2002 | Pathak et al. |
| 2001/0024697 A1 | 9/2001 | Baron et al. |
| 2002/0004140 A1 * | 1/2002 | Swan et al. ................. 428/500 |

FOREIGN PATENT DOCUMENTS

| JP | 54060386 A * | 5/1979 | ................. 526/204 |
| WO | WO 03 055611 A1 | 7/2003 | |

OTHER PUBLICATIONS

Tazuke et al., "A Novel Modification of Polymer Surfaces by Photografting", American Chemical Society (1980), pp. 217-241.

* cited by examiner

*Primary Examiner*—Michael Barr
*Assistant Examiner*—Ryan Schiro
(74) *Attorney, Agent, or Firm*—Weingarten, Schurgin, Gagnebin & Lebovici LLP

(57) ABSTRACT

This invention concerns a method of immobilizing a polymer hydrogel on the surface of a corresponding polymer substrate, and a polymer substrate that has a polymer hydrogel layer immobilized, at least in areas, on its surface. The invention has applications particularly as a biocompatible hydrogel coating in the field of medical technology, for example as a coating for surfaces coming in contact with blood, as in hemodialysis, and as a coating for urinary catheters, venous catheters, stents and other surfaces.

14 Claims, No Drawings

METHOD FOR IMMOBILIZING HYDROGEL-FORMING POLYMERS ON POLYMER SUBSTRATE SURFACES

This application is a 371 national phase filing of PCT/EP2003/008180 filed Jul. 24, 2003, and claims priority to a German application No. 102 38 559.9 filed Aug. 22, 2002.

The invention relates to a method of immobilizing a polymer hydrogel on a corresponding polymer substrate surface, and a polymer substrate that has a polymer hydrogel layer immobilized on its surface, at least in some areas. The invention has applications particularly as a biocompatible hydrogel coating in the medical technology field, for example as a coating for surfaces in contact with blood, as in hemodialysis, and as a coating for urinary catheters, venous catheters, stents and other surfaces.

Hydrogel coatings are used to improve the biocompatibility of surfaces that come in contact with body fluids, especially blood. These types of hydrogel coatings are supposed to reduce cells and proteins occupying the surface that activate the body's own defense system against foreign materials and promote blood clotting. These types of hydrogel coatings are also applied to increase the ability of aqueous solutions to slide on the corresponding substrate and improve their wettability.

Known examples of hydrogels used for this are polyethylene glycol (PEG) and polyvinylpyrrolidone (PVP), which are already inserted in the matrix of the respective basic polymers when the corresponding medical technology products are produced. If the basic polymers in molten or dissolved form cannot be mixed with the hydrogel compounds, the substrate surfaces can be coated with them afterward.

There are various known methods of fixing of these types of hydrogels covalently to the substrate being treated. Thus, for example, short-term electromagnetic radiation in the γ-radiation or X-ray range is used to allow the hydrogels to be fixed even on surfaces that are not very chemically reactive. Frequently, reactive intermediate products are produced deep within the base polymer used. The color and the mechanical stability of the product can also be changed for the worse.

In purely chemical immobilizing methods, generally substrate materials that are not very reactive are activated by corrosive reagents like chlorosulfonic acid, for example, in order to then bond ligands to the surface to be coated. This produces technical production problems with corrosive or toxic reagents. But, in the case of polyvinylpyrrolidone, it has proven difficult to bond a corresponding hydrogel to polymer substrate surfaces like polypropylene (PP) or polyvinyl chloride (PVC), for example.

U.S. Pat. No. 6,159,645 describes a method of crosslinking polyvinylpyrrolidone in the production of picture tubes in the electronics industry, wherein the sodium salt of 4,4'-diazidostyrene-2,2-disulfonic acid is used as the photoinitiator. However, this sodium salt is a problem in the production of medical technology products for toxicological reasons.

Vitamin B2 (riboflavin) has long been known as a photoinitiator for the polymerization of reactive monomers like acrylamide or vinyl pyrrolidone (see U.S. Pat. No. 2,850,445). After UV radiation of the monomer-initiator mixture in a homogeneous solution, the corresponding hydrogels are formed, which precipitate, especially when crosslinked. The US patent above provides for the formation of hydrogels from monomer units. It is known how to initiate polymerization with vitamin B2 as the photoinitiator, especially in the field of biochemical analysis. Here, the polyacrylamide gels produced thereby are used as a matrix for electrophoretic separation of proteins. With highly sensitive proteins, the more commonly used ammonium peroxodisulfate (APS)/N,N,N',N'-tetramethylethylene diamine (TEMED) intiator system is replaced by riboflavin, since it is known to be especially gentle. This makes it possible, for example, to include living cells in a hydrogel matrix with riboflavin as the photoinitiator; see U.S. Pat. No. 6,224,893. In this method, mixtures of reactive monomers and polymers are used, which after reaction, form an interpenetrating network that contains the cells.

US 2002/0122872 A1 describes a method of coating the surface of a material using thioxanthone, for example, as the photoinitiator.

This invention is based on the problem of providing a simple, inexpensive and largely gentle method of immobilizing hydrogels on polymer surfaces. This type of method should cause no adverse changes in the polymer surface and use no toxicologically unsafe initiators, which affect worker safety during the production process or remain in the hydrogel layer produced as a contaminant.

This problem is solved by the embodiments characterized in the claims.

In particular, a method of immobilizing a polymer hydrogel on the surface of a polymer substrate is provided, wherein a composition including at least one hydrogel-forming polymer and at least one non-toxic photoinitiator compound is applied to the surface of a polymer substrate to form a hydrogel layer, at least in some areas of it, and then the hydrogel layer is subjected to treatment with electromagnetic radiation, so that the hydrogel is immobilized on the polymer substrate surface, forming a hydrogel layer on it. The invention thus provides for the immobilization or fixing of an already finished hydrogel on polymer surfaces, in contrast to the method common in the state of the art of producing a hydrogel from corresponding monomers. According to the invention, the immobilization of the hydrogel takes place after the polymer surface has already been physically coated with the hydrogel.

Preferably, the hydrogel-forming polymer is on a polyvinylpyrrolidone, polyalkylene glycol, polyvinyl alcohol, polyethylene imine or polyvinyl amine base, more preferably on a polyvinylpyrrolidone or polyalkylene glycol base, and most preferably on a polyvinylpyrrolidone base.

The polyvinylpyrrolidone (PVP)-based polymer includes polyvinylpyrrolidone, copolymers containing polyvinylpyrrolidone and derivatives of polyvinylpyrrolidone or its copolymers. The K value of the polyvinyl-pyrrolidone-based polymer is not subject to any specific limitation. Preferably, the polyvinylpyrrolidone-based polymer has a K value in the range from 15 to 120, especially preferred a K value of 120. The K value is a measure of the molecular weight (H. Fikentscher, Cellulose Chemistry 13 (1932), pages 58 to 64 and 71 to 74). The K value of polymers can be set using the starting amount, temperature and pH value under the polymerization conditions of the PVP polymer to be used in the invention. According to the invention, it is also possible to use copolymers containing polyvinylpyrrolidone. It is preferred that at least 50%, and more preferably 75% of the monomer units in these types of copolymers be vinyl pyrrolidone monomers. Vinyl acetate and vinyl ether can be comonomers, for example. The derivatives of polyvinylpyrrolidone can be derivatives, for example, that are capable of altering or modulating physiological reactions. This includes, in particular, compounds that can affect blood clotting or immune system function. Such polyvinylpyrrolidone derivatives include, for example, oligosaccharide-substituted PVP polymers and peptide-substituted PVP polymers. One example of this is the PVP heparin complex, as described in U.S. Pat. No. 4,239,664, for example, to which explicit reference is made here.

Examples of such polyvinylpyrrolidone derivatives are alkyl-substituted polymers, for example ($C_1$-$C_6$)-alkyl substituted derivatives of polyvinylpyrrolidone. Alkyl substitution can be both on the alkylene polymer basic frame and on the pyrrolidone ring.

The polyalkylene glycol-based polymer can be chosen from polyethylene glycol (PEG) or polypropylene glycol, for example.

Any polymers or copolymers commonly used in medical technology can be used as the polymer substrate to be provided with the hydrogel layer in the invention. Preferably, polymer materials made of polyethylene, polypropylene, polyvinyl chloride, polycarbonate or polyurethane or mixtures or copolymers of them can be used as the polymer substrate, to which a hydrogel layer will be applied according to the invention. SEBS polymer substrates can also be used for this, for example. The polymer substrate to be coated can be a dialyser, hose, catheter, stent or urinary catheter or at least a part of it.

The concentrations of hydrogel-forming polymer and initiator compound used in the hydrogel-forming composition are not subject to any specific limitation. The concentrations should, however, be high enough to guarantee the surface properties described and not form a hydrogel layer that can be washed out. The viscosity of the hydrogel-forming composition should be suited to the coating method to be used. The exact concentration to be used can be chosen by an expert. For example, when using a 1% to 10% solution by weight of polyvinylpyrrolidone (K value of 120) in ethanol or dimethyl acetamide, the amount of initiator compound usually used will be from 0.1% to 0.5% by weight in relation to the hydrogel-forming compound. The exact concentration depends on the solubility of the initiator and the hydrogel-forming polymer in the respective solvent used.

Usually, the hydrogel-forming composition contains one or more solvents besides at least one hydrogel-forming polymer and at least one initiator compound. The choice of solvent is not limited. For example, they can be methanol, ethanol, dimethyl acetamide, acetonitrile, etc. and mixtures of them. The initiator compound and the hydrogel-forming polymer should be soluble in the same solvent or solvent system in order to guarantee homogeneous distribution of the hydrogel-forming polymer and the initiator in the dried reactant layer.

In the method in the invention, at least one non-toxic photoinitiator compound is used to immobilize the corresponding hydrogel. A non-toxic or physiologically safe photoinitiator compound is understood as a compound with an LD50 (rat) of $\geq$500 mg/kg., better $\geq$950 mg/kg and best $\geq$2000 mg/kg. Preferably, the non-toxic photoinitiator compound is a compound chosen from the group consisting of flavins, flavones, flavonoids and their derivatives, as well as nicotinic acid amide (Vitamin B3) and its derivatives and thioxanthone. ($C_1$-$C_6$)alkyl- and ($C_1$-$C_6$) alkoxy derivatives substituted in the $N^{10}$ position and riboflavin can be the flavin derivatives. The flavone derivatives can be, for example rutin (quercetin-3-rutinosid) and morin (2',3,4',5,7-pentahydroxyflavone). The flavonoid derivatives can be, for example, compounds from the group of flavonols, lavanols, flavanons, antthocyanes and isoflavonoids, if they are physiologically safe. Especially preferred for use in this invention are riboflavin, rutin (Quercetin-3-rutinosid), morin (2',3,4'5,7-pentahydroxyflavone) and nicotinic acid amide; most preferred is nicotinic acid amide.

In this invention, it was found surprisingly that non-toxic photoinitiator compounds, like those chosen from the group consisting of flavins, flavones, flavonoids and their derivatives, as well as nicotinic acid and its derivatives and thioxanthone, are not only suited as photoinitiators for the polymerization of unsaturated monomers in homogeneous solution, but are also suited as photoinitiators for immobilizing already finished, polyvinyl-pyrrolidone-based, polyalkylene-glycol-based, polyvinyl-alcohol-based, polyethylene-imine-based or polyvinyl-amine-based polymer hydrogels on corresponding polymer surfaces. A hydrogel-forming composition of at least one hydrogel-forming polymer and at least one non-toxic photoinitiator compound, especially like one of those chosen from the group consisting of flavins, flavones, flavonoids and their derivatives and nicotinic acid and its derivatives and thioxanthone, is treated on a polymer surface with electromagnetic radiation, preferably in the ultraviolet to visible range of the spectrum. These types of hydrogel coatings produced according to the invention are then immobilized on the polymer substrate surface, i.e., cannot be removed from the polymer surface either by boiling water or by an autoclave process. Without being bonded to it, these properties may indicate a covalent bond of the hydrogel layer to the polymer surface, so that release of such polymers is minimized on contact with blood. The polymer substrate surface treated in this way becomes hydrophilic by the invention's application of this type of hydrogel, which can be seen, for example, in reduced surface tension and higher wettability with water.

By using riboflavin in particular as the photoinitiator, the invention has a special advantage in that the polymer substrate surface treated this way, when radiated with ultraviolet light, shows fluorescence, which can be used very favorably for quality control of the hydrogel coating. Without describing the mechanism on which this is theoretically based, the presence of fluorescence can indicate that the riboflavin used as the initiator compound in the invention whose fluorescence properties are known is incorporated into the hydrogel layer.

The simultaneous presence of the hydrogel-forming polymer in the hydrogel layer can be proven, for example, by using PVP-based polymers due to PVP's ability to form complexes with different dyes. Thus, an iodine/iodine-potassium solution, which is also known as Lugol's reagent, is known to form a brownish colored complex with PVP. The known Dragendorff reagent forms a complex that is an orange-brown color with PVP. Both color reactions are positive on surfaces coated with PVP/riboflavin, for example. If a coating composition or hydrogel-forming composition is used without a corresponding photoinitiator compound, no adhesive layer is obtained after UV radiation. If the initiator compound used in the invention is replaced with an APS/TEMED initiator system, no adhesive PVP-based hydrogel layer is obtained either, for example.

Another subject of the invention concerns a polymer substrate, which has a polymer hydrogel layer immobilized, at least in some areas, on its surface, whereby the hydrogel layer also contains at least one non-toxic photoinitiator compound, preferably one of those chosen from the group consisting of flavins, flavones, flavonoids and their derivatives, as well as nicotinic acid amide and its derivatives and thioxanthone. Such a polymer substrate can be obtained by the method in the invention. The polymer materials above can be used as the polymer substrate. The polymer substrate to be coated can be a dialyser, hose, catheter, stent or urinary catheter or at least part of one.

The invention will be explained in greater detail with reference to the following examples.

EXAMPLES

Example 1

Riboflavin (Sigma, R-7649, EC NO 201-5071) was dissolved in absolute ethanol until saturated at room temperature, and the non-dissolved portions were filtered off. PVP K120 (ISP) 4% by weight was dissolved in this solution. This coating solution was applied to polymer surfaces and after drying was radiated with a UV-VIS light with a wavelength of 170 to 600 nm (machine: Fusion 300, Lamp D for radiation) for 1 to 120 seconds. The distance to the UV-VIS lamp was 100 mm. The surfaces were then boiled in distilled water for 60 minutes or steamed 40 minutes at 121° C. The hydrogel layer could then be detected by its fluorescence or dyeing capacity with an iodine/iodine-potassium or Dragendorff reagent.

Neither the choice of the solvent nor the choice of the PVP-based polymer is limited. Other solvents like dimethyl acetamide (DMAC) and mixtures of it or PVP polymers with other K values can also be used.

Example 2

A hydrogel-forming coating solution produced as in Example 1 using DMAC as the solvent was applied by a Tampoprint stamping machine to the polyurethane casting compound of a hemodialyser and dried in heat. After UV-VIS radiation, a PVP hydrogel layer could be detected on the polymer surface that was autoclavable, i.e., was not removed from the polymer substrate surface by an autoclave process.

Example 3

A hydrogel-forming coating solution produced as in Example 1 using ethanol as the solvent was evenly distributed by a spin-coating method on the inside of the dialysate cap (area with blood contact) of a hemodialyzer, dried and then radiated with UV-VIS light. The dialysate cap material was polypropylene or polycarbonate, which was activated, in this case, by corona treatment before the hydrogel-forming solution was applied. After UV-VIS radiation, a PVP hydrogel layer could be detected on the polymer surface, which was autoclavable, i.e., not removed from the surface of the polymer substrate by an autoclave process or by boiling with water.

Example 4

Morin (2',3,4',5,7-pentahydroxyflavone) was dissolved in absolute ethanol at room temperature until saturated, and the parts not dissolved were filtered off. PVP K120 (ISP), 4% by weight, was dissolved in this solution. This coating solution was applied to polymer surfaces and after drying was radiated with UV-VIS light with a wavelength of 170 to 600 nm (machine: Fusion 300, Lamp D for radiation) for 1 to 120 seconds. The distance from the UV-VIS lamp was 100 mm. The surfaces were then boiled in distilled water for 60 minutes or steamed 40 minutes at 121° C. The resulting surfaces were hydrophilic and could be stained with Dragendorff reagent.

Neither the choice of solvent nor the choice of PVP-based polymer is limited. Other solvents, like dimethyl acetamide (DMAC) and mixtures of it or PVP polymers with other K values can also be used.

Example 5

Rutin (Quercetin-3 rutinosid) was dissolved in absolute ethanol at room temperature until saturated, and the parts not dissolved were filtered off. PVP K120 (ISP), 4% by weight, was dissolved in this solution. This coating solution was applied to polymer surfaces and after drying was radiated with UV-VIS light with a wavelength of 170 to 600 nm (machine: Fusion 300, Lamp D for radiation) for 1 to 120 seconds. The distance from the UV-VIS lamp was 100 mm. The surfaces were then boiled in distilled water for 60 minutes or steamed for 40 minutes at 121° C. The resulting surfaces were hydrophilic and could be stained with Dragendorff reagent.

Neither the choice of solvent nor the choice of PVP-based polymer is limited. Other solvents, like dimethyl acetamide (DMAC) and mixtures of it or PVP polymers with other K values can also be used.

Example 6

A 4% PVP K120 (ISP)/isopropanol solution was made. Then, 0.33 g nicotinic acid amide was dissolved in 100 g of the solution. This coating solution was applied to polymer surfaces and after drying was radiated with UV-VIS light with a wavelength of 170 to 600 nm (machine: Fusion 300, Lamp D for radiation) for 1 to 60 seconds in the lamp lens. The distance from the UV-VIS lamp was 100 mm. The surfaces were then boiled in distilled water for 60 minutes or steamed for 40 minutes at 121° C. The resulting surfaces were hydrophilic and could be stained with Dragendorff reagent.

Neither the choice of solvent nor the choice of PVP-based polymer is limited. Other solvents, like dimethyl acetamide (DMAC) and mixtures of it or PVP polymers with other K values can also be used.

A hose made of polyvinyl chloride or polypropylene was then filled with the hydrogel-forming coating solution produced in Example 6 with ethanol and after it was removed was dried in a thin layer. After UV-VIS radiation, a PVP hydrogel layer could be detected on the polymer surface that was autoclavable, i.e., could not be removed from the inner surface of the hose by an autoclave process or by boiling with water for 1 h.

The method in the invention is not limited to hoses with a certain geometry or a certain material composition. Basically, any material on which a hydrogel layer with the properties described can be immobilized as described can be considered. The precondition is the accessibility of the PVP polymer/initiator reactant layer for the wavelength used and the ability to achieve a high enough intensity of electromagnetic radiation. Besides the hydrogel layer inside a hose, a hydrogel layer on the outside of a hose can naturally also be produced.

Example 7

A 4% PVP K120 (ISP)/isopropanol solution was produced. Then, 0.33 g thioxanthone was dissolved in 100 g of that solution. This coating solution was applied to polymer surfaces and after drying was radiated with UV-VIS light with a wavelength of 170 to 600 nm (machine: Fusion 300, Lamp D for radiation) for 1 to 60 seconds in the lamp lens. The distance from the UV-VIS lamp was 100 mm. The surfaces were then boiled in distilled water for 60 minutes or steamed for 40 minutes at 121° C. The resulting surfaces were hydrophilic and could be stained with Dragendorff reagent.

Neither the choice of solvent nor the choice of PVP-based polymer is limited. Other solvents, like dimethyl acetamide (DMAC) and mixtures of it or PVP polymers with other K values can also be used.

The invention claimed is:

1. A method of immobilizing a polymer hydrogel to the surface of a polymer substrate, whereby a composition consisting essentially of one or more hydrogel-forming polymers, at least one non-toxic photoinitiator compound, and one or more solvents is applied in direct contact with the surface of a polymer substrate to form a hydrogel layer at least in areas, and then the finished, as applied hydrogel layer is subjected to treatment with electromagnetic radiation, so that the hydrogel is immobilized to the surface of the polymer substrate, forming an immobilized hydrogel layer.

2. The method in claim 1, whereby electromagnetic radiation in the range from 170 nm to 600 nm is used for immobilization.

3. The method in claim 1, whereby the hydrogel-forming polymer is polyvinylpyrrolidone-based, polyalkylene-glycol-based, polyvinyl-alcohol-based, polyethylenei-mine-based or polyvinyl-amine-based.

4. The method in claim 3, whereby the polyvinylpyrrolidone-based polymer contains copolymers containing polyvinylpyrrolidone, derivatives of polyvinylpyrrolidone and their copolymers.

5. The method in claim 1, whereby the polymer substrate is made of a polymer material chosen from polyethylene, polypropylene, polyvinyl chloride, polycarbonate, SEBS or polyurethane or mixtures thereof.

6. The method in claim 1, whereby the polymer substrate is a dialyser, hose, catheter, stent or urinary catheter or at least part of one.

7. The method in claim 1, whereby the non-toxic photoinitiator compound is chosen from the group composed of flavins, flavones, flavonoids and their derivatives, as well as nicotinic acid amide and its derivatives and thioxanthone.

8. The method in claim 7, whereby the initiator compound is riboflavin, morin, rutin or a mixture thereof.

9. The method in claim 7, whereby the initiator compound is nicotinic acid amide.

10. The method in claim 7, whereby the initiator compound is thioxanthone.

11. The method in claim 2, whereby:
the hydrogel-forming polymer is polyvinylpyrrolidone-based, polyalkylene-glycol-based, polyvinyl-alcohol-based, polyethylene-imine-based or polyvinyl-amine-based;
the polyvinylpyrrolidone-based polymer contains copolymers containing polyvinylpyrrolidone, derivatives of polyvinylpyrrolidone and their copolymers;
the polymer substrate is made of a polymer material chosen from polyethylene, polypropylene, polyvinyl chloride, polycarbonate, SEBS or polyurethane or mixtures thereof;
the polymer substrate is a dialyser, hose, catheter, stent or urinary catheter or at least part of one;
the non-toxic photoinitiator compound is chosen from the group composed of flavins, flavones, flavonoids and their derivatives, as well as nicotinic acid amide and its derivatives and thioxanthone.

12. The method in claim 11, whereby the initiator compound is riboflavin, morin, rutin or a mixture thereof.

13. The method in claim 11, whereby the initiator compound is nicotinic acid amide.

14. The method in claim 11, whereby the initiator compound is thioxanthone.

* * * * *

UNITED STATES PATENT AND TRADEMARK OFFICE
CERTIFICATE OF CORRECTION

PATENT NO. : 7,572,489 B2
APPLICATION NO. : 10/522093
DATED : August 11, 2009
INVENTOR(S) : Stefan Dröschel It is certified that error appears in the above-identified patent and that said Letters Patent is hereby corrected as shown below:

Column 7, claim 3, line 24, "polyethylenei-mine-" should read -- polyethylene-imine- --.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,489 B2 | Page 1 of 1 |
| APPLICATION NO. | : 10/522093 | |
| DATED | : August 11, 2009 | |
| INVENTOR(S) | : Dröschel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1091 days.

Signed and Sealed this

Seventh Day of September, 2010

David J. Kappos
*Director of the United States Patent and Trademark Office*